United States Patent
Shroff et al.

(10) Patent No.: US 9,288,979 B2
(45) Date of Patent: Mar. 22, 2016

(54) MICROENCAPSULATED PENDIMETHALIN COMPRISING ALKALI OR ALKALINE EARTH METAL SALT OF ORGANIC ACID

(75) Inventors: Jaidev Rajnikant Shroff, Mumbai (IN); Vikram Rajnikant Shroff, Mumbai (IN); Prakash Mahadev Jadhav, Mumbai (IN); Christian Becker, King of Prussia, PA (US)

(73) Assignee: United Phosphorus Limited, Gujarat (IN)

( * ) Notice: Subject to any disclaimer, the term of this patent is extended or adjusted under 35 U.S.C. 154(b) by 245 days.

(21) Appl. No.: 13/576,181

(22) PCT Filed: Jan. 31, 2011

(86) PCT No.: PCT/IB2011/000144
§ 371 (c)(1),
(2), (4) Date: Jul. 31, 2012

(87) PCT Pub. No.: WO2011/095859
PCT Pub. Date: Aug. 11, 2011

(65) Prior Publication Data
US 2012/0309627 A1 Dec. 6, 2012

(30) Foreign Application Priority Data

Feb. 3, 2010 (IN) ............... 284/MUM/2010

(51) Int. Cl.
*A01N 33/18* (2006.01)
*A01P 13/00* (2006.01)
*B01J 13/18* (2006.01)
*A01N 25/28* (2006.01)

(52) U.S. Cl.
CPC ............... *A01N 33/18* (2013.01); *A01N 25/28* (2013.01)

(58) Field of Classification Search
None
See application file for complete search history.

(56) References Cited

U.S. PATENT DOCUMENTS

| 5,705,174 A | 1/1998 | Benoff |
| 2008/0207445 A1* | 8/2008 | Dexter et al. ............ 504/100 |

FOREIGN PATENT DOCUMENTS

| WO | 2004008852 | 1/2004 |
| WO | 2004089088 | 10/2004 |
| WO | 2010070096 | 6/2010 |

OTHER PUBLICATIONS

Cheng et al., Journal of Colloid and Interface Science, 305: 175-182 (2007).*

* cited by examiner

*Primary Examiner* — Kortney L Klinkel
*Assistant Examiner* — Lisbeth C Robinson
(74) *Attorney, Agent, or Firm* — Merchant & Gould P.C.

(57) ABSTRACT

A microencapsulated formulation of pendimethalin comprising an alkali or an alkaline earth metal salt of an organic acid. Also described are processes for the preparation of the formulation and a method of controlling weeds at a location by using the described formulation.

18 Claims, 7 Drawing Sheets

MICROENCAPSULATED PENDIMETHALIN COMPRISING ALKALI OR ALKALINE EARTH METAL SALT OF ORGANIC ACID

FIELD OF INVENTION

The present invention relates to a capsule suspension formulation comprising pendimethalin. More particularly, the present invention relates to a storage stable, improved non-staining capsule suspension formulation comprising pendimethalin.

BACKGROUND AND PRIOR ART

Pendimethalin is a dinitroaniline herbicide having chemical formula [n-(1-ethylpropyl)-3,4-dimethyl-2,6-dinitrobenzenamine). It was first registered for use in the United States in 1974. It is a selective herbicide which controls certain broadleaf weeds and grassy weed species in crop and non-crop areas. It is applied to soil preplant, preemergence, and postemergence with ground and aerial equipment.

Pendimethalin is an orange yellow crystalline solid with a melting point of 54-58° C. It is soluble in chlorinated hydrocarbons and aromatic solvents such as methylene chloride, acetone and xylene. Pendimethalin is stable under acidic and alkaline conditions.

Pendimethalin is currently available in various different agrochemical formulation types such as emulsifiable concentrate (21.9% to 42.3%), liquid (34.4%), granular (0.7% to 2.0%), soluble concentrate/liquid (22.0%), water dispersible granules, dry flowable (up to 60.0%), capsule suspension and wettable powder (50.0%). Thus, there are many formulation choices available to a formulator setting out to prepare a desired formulation of pendimethalin.

The different formulations applicable to an agrochemical differ in their effectiveness on the desired weeds, effects the tolerance of the turf and ornamentals to the herbicide, differ in their cost advantages, differ in the drift potential of the herbicide and also differ in the ease of application and compatibility with the application equipment. Another challenge to the skilled formulator is the selection of an appropriate surfactant. Surfactants are known to increase the rate of absorption of the herbicide in the weedy species but also increase the potential for plant injury to the desirable plants during herbicide drift. Yet another challenge before a skilled formulator setting out to obtain a formulation containing pendimethalin is selecting either a granular or a sprayable formulation.

Pendimethalin has been conventionally available in both granular and sprayable forms, which may differ in the degree of weed control. However, it is often advantageous to obtain a sprayable formulation containing certain herbicides due to inherent advantages of a sprayable formulation.

The granular formulations exhibit relatively low foliar absorption because most of the applied granules fall through the leaf canopy to the soil below. In contrast, sprayable products achieve good coverage and adhere better to the foliage, providing relatively good weed control. It has also been observed that a granular product comprises a greater relative amount of the inert ingredients comparative to a sprayable formulation. Thus, the amount of the formulated product to deliver the same dosage of the active ingredient is much greater with granules resulting in higher shipping and packaging costs.

An advantage of the sprayable formulation over granules is more uniform application achieved with the sprayable formulations. The granular formulations are usually difficult to apply uniformly, especially those that contain a relatively high concentration of active ingredient. Thus, it is more often advantageous to formulate sprayable formulations of certain agrochemicals.

However, phytotoxicity of some of the sprayable formulations including pendimethalin has been reported. It is desirable to provide formulations containing pendimethalin that do not display or reduces the extent of phytotoxicity.

Another challenge that relates to dinitroaniline herbicides, pendimethalin in particular, is the potential for staining the sidewalks and other locations where the herbicide is applied. The active ingredient herbicides of the dinitroaniline class have a yellowish or yellowish-orange color. It is further known that granular formulations often do not stain badly, whereas a liquid formulation may cause more serious staining. Moreover, granules are easy to sweep or blow from concrete surfaces, whereas overspray need to be washed off before it dries. Thus, it is desirable to provide sprayable formulations containing pendimethalin that substantially reduce the incidence of staining.

U.S. Pat. No. 4,871,392, discusses under the background thereof, that pendimethalin is known to exist in polymorphic forms as orange and yellow crystals. This patent further discusses that pendimethalin is a pesticide that is difficult to formulate owing partly due to the unique staining problems associated with pendimethalin. This patent further discusses that the presence of pendimethalin in the orange macrocrystal form results in large elongated crystals in final formulations. Moreover, when pendimethalin in the orange macrocrystal form is found in compositions, very large, elongated crystals (about 3000 microns in length) appear in final product, resulting in instability, difficulty in processing and unreliability of usage apart from the severe staining further compounded by a severe clogging of nozzles.

U.S. Pat. No. 5,705,174 discloses microencapsulated pendimethalin formulations i.e. an aqueous concentrate composition of pendimethalin particles which are encapsulated by a polymeric wall material, which show a reduced tendency to form large crystals. These compositions also have improved storage stability. Unfortunately, it has been seen that microencapsulation of pendimethalin tends to slow the release of the active ingredient.

U.S. Pat. No. '174 teaches an aqueous capsule suspension formulation of pendimethalin, which contains about 456 grams of active ingredient per liter. The encapsulation of pendimethalin allows for the elimination of organic solvents in the product. The elimination of organic solvents reduces odor, staining to a certain extent, volatility and surface residue adhesion as compared to existing emulsifiable concentrate formulations of pendimethalin. Moreover, the microencapsulated pendimethalin formulation is stable under conditions of freezing and thawing and is compatible with liquid and dry fertilizer. However, the existing problem of staining, phytotoxicity and corrosiveness is not adequately addressed by the disclosure of U.S. Pat. No. 5,705,174.

Moreover, this patent essentially teaches a microencapsulated formulation of pendimethalin containing an inorganic salt, which is added prior to microcapsule formation. It is disclosed that the addition of an inorganic salt or mixtures thereof prior to the microcapsule formation provides a visibly cleaner microcapsule as more of the colored active ingredient is encapsulated, which is therefore unable to stain the external surfaces of the microcapsules. These microcapsules are also stated to be less prone to breakage than the microcapsules prepared by the conventional methods. Examples of inorganic salts taught by this patent are sodium chloride, calcium chloride, potassium chloride, sodium nitrate, magnesium sulfate and/or sodium sulfate.

However, these inorganic salts are not without additional disadvantages. The use of an inorganic salt such as sodium chloride even to the extent of 0.1-0.5% has been shown to aggravate the already existing phytotoxicity of pendimethalin. Sodium and chloride ions contribute synergistically to salt toxicity in wheat, Biologia Plantarium, 37 (2); 265-271, 1995, Martin et al., studied the effects of supplying excess mineral salts, involving sodium as a cation and a range of counter-anions, including chloride on the growth and photosynthetic capacity of a salt susceptible bread wheat. It was found that the synergistic effect of sodium and other alkali and alkaline earth metals with chlorine shows that neither of these ions is alone responsible for the salt stress induced damage in plants.

Moreover, these inorganic salts dissociate and/or dissolve in water and increase the hardness of water. The increased water hardness further reduces the temperature and suspension stability of microencapsulated pendimethalin. Moreover, the polymeric capsule wall of the disclosed microencapsulated pendimethalin is still susceptible to breakage to an appreciable extent. Thus, the problem of staining continues to plague the existing state of the art.

A need remains in the art for microencapsulated formulations of pendimethalin having improved non-staining property with reduced phytotoxicity problems. The present invention adequately addresses these and other needs existing in the art.

Advantages of the Invention

Thus, an advantage of the present invention is a capsule suspension formulation of pendimethalin that does not demonstrate any phytotoxicity to the desirable plants.

Another advantage of the present invention is a capsule suspension formulation of pendirnethalin that is substantially non-staining.

Yet another advantage of the present invention is a capsule suspension formulation of pendimethalin which shows a reduced tendency to form large crystals.

Another advantage of the present invention is a capsule suspension formulation of pendimethalin that is storage stable.

Yet another advantage of the present invention is a capsule suspension formulation of pendimethalin that is stable under conditions of freezing and thawing.

Another advantage of the present invention is a capsule suspension formulation of pendimethalin that does not suffer from capsule polymeric wall rupture.

Yet another advantage of the present invention is a capsule suspension formulation of pendimethalin that does not increase the hardness of water.

Yet another advantage of the present invention is a capsule suspension formulation of pendimethalin that does not appreciably corrode the container.

Another advantage of the present invention is a capsule suspension formulation of pendimethalin that avoids the need for an inorganic salt or mixtures thereof.

The remaining portion of the description and claims offers at least one of these and other advantages.

SUMMARY OF THE INVENTION

Thus, in one aspect, the present invention provides a capsule suspension formulation of pendimethalin comprising a herbicidally effective amount of microencapsulated pendimethalin, the microcapsules comprising said herbicidally effective amount of pendimethalin being encapsulated within a polymeric wall, said polymeric wall being in-situ formed by an interfacial polymerization reaction occurring between a first phase dispersed in a second phase, at least one of said first and second phases being characterized in comprising a pre-defined amount of at least one alkali or alkaline earth metal salt of an organic acid.

In another aspect, the present invention provides a process for the preparation of a capsule suspension formulation, said process comprising:
(a) forming an aqueous solution comprising at least one surfactant and a pre-defined amount of at least one alkali or alkaline earth metal salt of an organic acid;
(b) forming an organic phase by melting a herbicidally effective amount of pendimethalin active ingredient and adding a predetermined amount of polyisocyanate wall forming component;
(c) dispersing said organic phase in said aqueous solution to obtain an emulsion to form an interface between the discrete droplets of organic phase and the aqueous phase; and
(d) maintaining said emulsion for a sufficient period of time to allow substantial completion of the self-polymerization reaction of polyisocyanate such that said liquid droplets in the organic phase are converted to capsules comprising polyurea shells enclosing pendimethalin active ingredient.

In another aspect, the present invention provides a process for the preparation of a capsule suspension formulation, said process comprising:
(a) forming an aqueous solution comprising at least one surfactant and a pre-defined amount of at least one alkali or alkaline earth metal salt of an organic acid;
(b) forming an organic phase by melting a herbicidally effective amount of pendimethalin active ingredient and adding a predetermined amount of a first wall component to said organic phase;
(c) dispersing said organic phase in said aqueous solution to obtain an emulsion; and
(d) adding a second wall forming component to said emulsion such that said second wall forming component reacts with said first wall forming component comprised within said emulsion to polymeric wall encapsulating at least said herbicidally effective amount of pendimethalin active ingredient.

DESCRIPTION OF INVENTION

It has been surprisingly found that the presence of an alkali or alkaline earth metal salt of an organic acid within the microencapsulated formulation of pendimethalin provides a substantially non-staining formulation. The term "substantially non-staining" herein denotes that such formulations comprising an alkali or alkaline earth metal salt of an organic acid demonstrates surprisingly reduced staining property by a fraction of at least two to about five times in comparison with the conventional formulations comprising an inorganic salt.

It has further been found that the microencapsulated formulations according to the present invention comprising an alkali or alkaline earth metal salt of an organic acid also reduce or eliminate the phytotoxicity that was observed with conventional formulations comprising an inorganic salt. Moreover, the addition of an alkali or alkaline earth metal salt of an organic acid does not increase the hardness of water which was observed with the conventional formulations thereby enhancing the suspension stability of the resultant formulations. It was surprising that use of an organic salt of an alkali or alkaline earth metal led to a drastic improvement in the suspension stability of the formulations according to the present invention. The present inventors have further found that the presence of an inorganic salt was shown to corrode the container while an organic salt did not corrode the container in which it was placed. The formulations according to the present invention were found to be storage stable. Without wishing to be bound by theory, it is believed that the presence of an alkali or alkaline earth metal salt of an organic acid further prevents the early rupture of the polymeric capsule wall.

Accordingly, in one aspect, the present invention provides a capsule suspension formulation of pendimethalin comprising a herbicidally effective amount of microencapsulated pendimethalin, said microcapsules comprising said herbicidally effective amount of pendimethalin encapsulated within a polymeric wall, said polymeric wall being in-situ formed by an interfacial polymerization reaction occurring between an organic phase dispersed in an aqueous phase, said aqueous phase being characterized in comprising a pre-defined amount of at least one alkali or alkaline earth metal salt of an organic acid.

It should be understood however that said aqueous and organic phases are not particularly limiting. The interfacial polymerization reactions suitable for encapsulated formulations according to the present invention may be prepared by reaction between the wall forming components present in two substantially immiscible liquids, of which said organic and aqueous phases constitute a preferred embodiment. Moreover, the two walls forming components may be either same or different.

In another aspect, the present invention provides a process for the preparation of a capsule suspension formulation, said process comprising:
  (a) forming an aqueous solution comprising at least one surfactant and a pre-defined amount of at least one alkali or alkaline earth metal salt of an organic acid;
  (b) forming an organic phase by melting a herbicidally effective amount of pendimethalin active ingredient and adding a predetermined amount of a first wall component to said organic phase;
  (c) dispersing said organic phase in said aqueous solution to obtain an emulsion; and
  (d) adding a second wall forming component to said emulsion such that said second wall forming component reacts with said first wall forming component comprised within said emulsion to polymeric wall encapsulating at least said herbicidally effective amount of pendimethalin active ingredient.

The capsule polymeric wall of the present invention may be any known shell wall material and is preferably selected from a polyurea, a polyurethane, a polyamide, a polycarbonate, a polysulfonamide shell wall or a crosslinked or non-crosslinked combinations thereof. Preferably, the capsule polymeric wall is a polyurea wall.

The capsule polymeric wall of the present invention is formed using interfacial polymerization by contacting said first wall forming component with a second wall forming component as is conventionally known in the art.

The first wall forming component is preferably selected from a polyisocyanate, a polyacid chloride, a polychloroformate and a polysulfonyl chloride. The second wall forming component is preferably selected from a polyamine and polyol. Preferably, a polyisocyanate reacts with a polyamine to form a polyurea capsule wall of the present invention.

The preferred polyisocyanates as the first wall forming component may be selected from tetramethylene diisocyanate, pentamethylene diisocyanate, hexamethylene diisocyanate, toluene diisocyanate, diphenylmethene-4,4'-diisocyanate, polymethylene polyphenylene isocyanate, 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4'4"-triphenylmethane triisocyanate. A preferred polyisocyanate first wall forming component is polymethylene polyphenylisocyanante.

The preferred polyamines as the second wall forming components may be selected from ethylenediamine, propylene-1,3-diamine, tetramethylenediamine, pentamethylenediamine, 1,6-hexamethylenediamine, diethylenetriamine, triethylenetetramine, tetraethylenepentamine, pentaethylenehexamine, 4,9-dioxadodecane-1,12-diamine, 1,3-phenylenediamine, 2,4- and 2,6-toluenediamine and 4,4'-diaminodiphenylmethane or acid addition salt thereof. The preferred polyamine according to the present invention is diethylenetriamine.

The first wall forming component comprises from about 0.1% to about 20% by weight of the organic phase of the present invention. The second wall forming component is preferably present in an amount of about 0.3% to 7.5% by weight relative to the total weight of the formulation.

In a further preferred embodiment, the preferred polyurea polymeric shell wall may be formed by a self-condensation reaction of a polyisocyanate wall forming component. In this embodiment, the process for the preparation of the capsule suspension formulation according to the present invention comprises establishing a physical dispersion of an organic phase in the aqueous phase. In this embodiment, the organic phase comprises the organic isocyanate intermediate such as hereinabove described along with the pendimethalin active ingredient.

Thus, in another aspect, the present invention provides a process for the preparation of a capsule suspension formulation, said process comprising:
  (a) forming an aqueous solution comprising at least one surfactant and a pre-defined amount of at least one alkali or alkaline earth metal salt of an organic acid;

(b) forming an organic phase by melting a herbicidally effective amount of pendimethalin active ingredient and adding a predetermined amount of polyisocyanate wall forming component;

(c) dispersing said organic phase in said aqueous solution to obtain an emulsion to form an interface between the discrete droplets of organic phase and the aqueous phase; and (d) maintaining said emulsion for a sufficient period of time to allow substantial completion of the self-polymerization reaction of polyisocyanate such that said liquid droplets in the organic phase are converted to capsules comprising polyurea shells enclosing pendimethalin active ingredient.

In an embodiment, the emulsion of said organic phase in said aqueous solution may be preferably heated to a temperature of between 20° C. to about 100° C., preferably to about 35-85° C. to accelerate the self-condensation of the polyisocyanate pre-polymer.

However, irrespective of whether self condensation of the first wall forming component is preferred or condensation between a first and a second wall forming component is preferred, the relative quantities of the organic and the aqueous phases are not critical for the process of the present invention. Typically, the organic phase may comprise upto about 75% by volume of the total emulsion and comprises discrete droplets of an organic solution dispersed in the aqueous solution.

The droplet size in the emulsion was not found critical to the formulation and process of the present invention but may be found between 0.5 microns to about 4000 microns, which may be further adapted using a high shear device to preferably about 1 micron to about 100 microns. It has further been found that the in situ self condensation polymerization reaction is self terminating and is generally allowed to run to completion. The reaction typically runs to completion within the span of a few minutes to a few hours. In a preferred embodiment, the reaction is typically allowed to run for about 2 to 3 hours.

However, the preferred polyurea polymeric shell may be formed by a self-condensation reaction of a preferred polyisocyanate using other preferred methods. In one such preferred embodiment, the formation of the polyurea capsule enclosure around the dispersed organic droplets could be brought about by (a) dispersing the organic phase droplets in the continuous aqueous phase to form an emulsion followed by heating the emulsion resulting therefrom; or (b) heating the continuous aqueous phase and dispersing the organic phase droplets in the heated continuous aqueous phase to form the emulsion thereby effecting the desired self-condensation reaction at the interface between the organic droplets and the aqueous phase.

The alkali or alkaline earth metal salt of an organic acid as used herein is preferably selected from alkali or alkaline earth metal salt of a weak organic acid selected from acetic acid, propionic acid, citric acid, fumaric acid, tartaric acid, oxalic acid, succinic acid, valeric acid, malonic acid, glutaric acid, adipic acid and phthalic acid.

The preferred alkali metal is selected from sodium and potassium. In a more preferred embodiment, the preferred alkali metal is sodium.

In another preferred embodiment, the alkali or alkaline earth metal salt of an organic acid is selected from sodium acetate or disodium succinate.

The aqueous solution comprises at least one surfactant. Preferably, the surfactant may be selected from the group comprising ethoxylated lignosulfonic acid salts, lignosulfonic acid salts, oxidized lignins, lignin salts, salts of styrene-maleic anhydride copolymers, polyvinyl alcohol, salts of partial esters of styrene-maleic anhydride copolymers, partial salts of polyacrylic acid and partial salts of polyacrylic acid terpolymers.

Preferably, the surfactant is lignosulfonate of calcium or sodium.

Preferably, the surfactant is present in an amount of about 0.2% to about 5% by weight of the formulation.

The aqueous solution of the present invention includes an alkali or alkaline earth metal salt of an organic acid or mixtures thereof in an amount of from about 2% to about 55% by weight of the formulation.

The term "herbicidally effective amount" of pendimethalin is that quantity of pendimethalin which when applied in that amount will provide the required control of weeds. The particular amount is dependent upon many factors including, for example, the crop, weeds sought to be controlled and environmental conditions. The selection of the proper quantity of active agent to be applied, however, is within the expertise of one skilled in the art and is not considered particularly limiting.

The microencapsulated formulations according to the present invention comprise from about 5% to about 60% of pendimethalin active ingredient.

In a preferred embodiment, the polymeric shell wall according to the present invention constitutes from about 1% by weight to about 20% by weight of the formulation. In another preferred embodiment, the polymeric shell wall constitutes about 2.5% by total weight of the formulation.

The microcapsules of the present invention preferably have a particle size of about 2 micrometers to 50 micrometers.

Preferably, the capsule suspension formulations of the present invention comprise an anti-foam in an amount of about 0.01% to about 5% by weight of the formulation. Such suitable anti-foams are conventionally known in the art and are not particularly limiting.

The capsule suspension of the present invention may further include a rheology modifier. The preferred rheology modifier includes xanthan gum and clay, which may be present in an amount of about 0.01% to about 3% by weight of the formulation.

The capsule suspension formulation according to the present invention may further be neutralized with a mineral acid to regulate the pH within the desired range. Accordingly, the formulations according to the present invention additional comprises from about 0.1% to about 10% of a neutralizing acid, which may be a mineral or an organic acid. Preferably, the mineral acid is hydrochloric acid.

Another advantage of the addition of a neutralizing acid is that the added acid combines with the unreacted amines to form an ammonium salt, which substantially reduces the amount of external salt addition required for achieving an appreciable non-staining property. The addition of a neutralizing acid is particularly beneficial in reducing the level of inorganic salt of the prior art formulations, which has been reported to aggravate the problem of phytotoxicity in various tested plants. In this embodiment of the present invention, a significantly large quantity of amines in excess may be employed to further reduce the external addition of a salt by in situ generation of a larger amount of salt upon reaction with the neutralizing acid.

In a preferred embodiment, the formulations according to the present invention may additionally comprise a biocide in an amount of from about 0.01% to about 3% by weight of the formulation.

In another aspect, the present invention also provides a process for the preparation of a capsule suspension formulation, said process comprising:
(a) forming an aqueous solution comprising at least one surfactant and a pre-defined amount of at least one alkali or alkaline earth metal salt of an organic acid and optionally heating said aqueous solution;
(b) forming an organic phase by melting a herbicidally effective amount of pendimethalin active ingredient and adding a predetermined amount of a first wall component to said organic phase;
(c) dispersing said organic phase in said aqueous solution to obtain an emulsion and optionally heating said formed emulsion; and
(d) adding a second wall forming component to said emulsion such that said second wall forming component reacts with said first wall forming component comprised within said emulsion to polymeric wall encapsulating at least said herbicidally effective amount of pendimethalin active ingredient.

Preferably, said step of forming an aqueous solution comprises heating tap water to an elevated temperature, preferably about 60° C. and adding said surfactant and said alkali or alkaline earth salt of an organic acid. In a preferred embodiment, an anti-foam is also added to said aqueous solution.

In another preferred embodiment, said first wall forming component is preferably added to said molten pendimethalin while stirring.

In yet another preferred embodiment, said step of dispersing said organic phase in said aqueous solution to obtain an emulsion is carried out to a desired particle size.

In another preferred embodiment, subsequent to the addition of the second wall forming component to the emulsion, the reaction is allowed to continue for a predetermined time, preferably one hour under stirring while the reaction is maintained at an elevated temperature.

Subsequently, the reaction mixture is neutralized with an inorganic acid, preferably hydrochloric acid. The neutralization is carried out preferably to attain a formulation pH of from about 6.5 to about 7.5.

Subsequently, xanthan gum is preferably added under stirring.

In a preferred embodiment, a biocide is added to obtain the target formulation.

In a preferred embodiment, the process of the present invention is carried out at an elevated temperature to maintain the pendimethalin active ingredient in a molten state and to enhance the rate of polymeric wall formation. In this embodiment, the process of the present invention is preferably carried out at a temperature of about 35° C. to about 85° C., and is more preferably conducted at a temperature of about 50° C. to 65° C.

The release rate of the formulations according to the present invention preferably varied from about 100 ng to about 145 ng, while the free active ingredient was measured from about 0% to about 0.2% by weight of the formulation.

The invention further relates to a method for controlling weeds at a locus by applying to the locus of the weeds a herbicidally effective amount of a microencapsulated pendimethalin according to the present invention or a capsule suspension formulation obtainable by the process of the present invention.

Preferably, the present invention provides a method for controlling undesirable plant species which comprises applying to the foliage of the plants or to the soil or water containing seeds or other propagating organs thereof, a herbicidally effective amount of a microencapsulated pendimethalin of the present invention or a capsule suspension formulation obtainable by the process of the present invention.

Yet another surprising advantage offered by the present invention was the substantial reduction in the corrosive property. The formulations according to the present invention did not require to be stored in non-aluminum or non-metallic or non-epoxy containers, which was a severe limitation on the packaging and transport of the prior marketed formulations.

Advantageously, the microcapsule formulations prepared according to the present invention or obtainable by the process of the present invention may be used directly as herbicidal compositions or may be diluted with water for use.

Alternatively, additional ingredients such as anti-settling agents, pH-adjusters, anti-freeze agents and the like may be added to the microcapsule compositions prepared by the process of the present invention to form concentrated microcapsule herbicidal compositions without departing from the scope of the present invention.

The invention shall now be described with reference to the following specific examples. It should be noted that the example(s) appended below illustrate rather than limit the invention. and that those skilled in the art will be able to design many alternative embodiments without departing from the scope of the present invention.

Examples 1, 2 and 3

An aqueous solution was created by heating tap water to 60° C. while adding sodium acetate, then sodium lignosulfonate, then antifoam while stirring. A sufficient quantity of water was separately preserved for the amine and gum preparations. Meanwhile, organic phase was formed by melting pendimethalin technical to 60° C. and then adding polymethylene polyphenylisocyanante while stirring. The aqueous and organic phases were maintained at 60° C. throughout reaction. The organic phase was emulsified in the aqueous solution till the desired particle size. DETA (amine) was added to the resultant emulsion. Reaction was allowed to proceed for 1 hour while maintaining heat at 60° C. under stirring. The reaction mixture was allowed to cool to ambient temperature for 15 minutes before neutralizing with HCl. The formulation was neutralized to pH 8.0 in cold conditions or at a pH of 7 in warmer conditions. The neutralized formulation was filtered through a 60 mesh sieve. A xanthan gum-water slurry was separately prepared and added to the above formulation under strong stirring conditions for at least 15 minutes to have a complete development of the gum. Lastly, a biocide was added. The particle size was measured using a Horiba LA-910. The resultant formulation was compared to the properties of conventionally marketed formulation.

Table 1 below is the composition of the formulation obtained by the process described in the above process.

| Phase | Component | For 47 g batch (Example 1) | For 100 g batch (Example 2) | For 2000 g batch (Example 3) |
|---|---|---|---|---|
| Water phase | Water | 50.09 | 102.339 | 2046.771 |
| | Sodium lignosulfonate | 1.22 | 2.481 | 49.612 |
| Oil phase | Pendimethalin technical | 48.91 | 100.000 | 2000.000 |
| | Polymethylene polyphenylisocyanante | 1.04 | 2.047 | 40.932 |
| Amines | DETA (x2) | 0.53 | 1.035 | 20.701 |
| Others | HCl (34-37%) | 1.24 | 2.530 | 50.605 |
| | Sodium acetate | 18.22 | 37.209 | 744.186 |

The properties of the formulation above were compared with the specification of the conventional formulation, which is commercially available and tabulated as hereunder in Table 2.

| Parameter | Commercially available formulation as per the disclosure of U.S. Pat. No. 5,705,174 | Formulation according to the present invention |
|---|---|---|
| Active ingredient (%) | 38.7 | 39.55 |
| Free AI (%) | 0.05 | 0.13 |
| Viscosity (cP) | 300 | 400-700 |
| Density (g/mL) | 1.16 | 1.17 |
| pH | 7.5 | 7.5 |
| Suspensibility (%) | 87-91 | 81-87 |
| Wet Sieve, 60 mesh (250 microns), residue | none (traces) | None (traces) |
| Staining on cloth tape (DE) | 11.22 | 2.44 |
| Staining on duct tape (DE) | 3.19 | 1.49 |

Staining Measurement

The staining measurements reported above were measured with the help of a Hunter LabScan XE colorimeter. Each reported test was repeated five times to confirm the staining or non-staining nature of the tested samples on different samples and under different testing conditions. In order to conclude the improvement in the non-staining properties of the formulations of the present invention, staining tests were conducted on duct tape and repeated to cloth tape to reconfirm the findings.

In the tests reported above, the colorimeter measured the staining color left on the substrate by assigning three values L*, a* and b* to the stain which corresponded to the lightness/darkness measurement, redness/greenness measurement and the yellowness/blueness measurement respectively. The differences between these measured for each tested sample i.e. that according to the present invention and the conventionally known sample and that of a standard sample were calculated as delta (Δ) values respectively:

Δa*=a* (sample)−a* (standard), wherein +Δa* meant sample was redder than standard and −Δa* meant the sample was greener than the standard;

Δb*=b* (sample)−b*(standard), wherein +Δb* meant the tested sample was yellower than standard and −Δb* meant the sample was bluer than standard;

ΔL*=L* (sample)−L*(standard), wherein +ΔL* meant the sample was lighter than the standard and −ΔL* meant the sample was darker than the standard.

The total color or staining value, ΔE, was thereafter calculated using the following formula:

$$\Delta E = SQRT[(\Delta L^*)^2+(\Delta a^*)^2+(\Delta b^*)^2]$$

A greater value of ΔE corresponded to a greater degree of staining. The stain samples were prepared on cloth tape (Scotch Glass Cloth Electrical Tape) or duct tape—(Tesa, BDF Beiersdorf White Duct Tape). These tapes were chosen in order to investigate possible differences in staining potential of the formulations on different surfaces. The substrates consisted of 2 inch by 2 inch (5 cm by 5 cm) squares cut from transparent paper with a piece of tape on the center. Enough formulation was applied to the tapes to create a ¾ inch (2 cm) diameter circle. The formulations were left on the tape for 15 minutes and then rinsed off completely with a water squirt bottle. Color/stain testing was then performed within 30 minutes of when samples were rinsed. Blank samples of tapes without formulation were tested first on the equipment to subtract out color values inherent to the tapes themselves. Stain samples were prepared in duplicate and each sample was measured twice, once in a horizontal orientation and once in a vertical orientation on the colorimeter to cancel the effects of the tape's directional grain. This yielded four data points for each stain sample. Therefore, the total staining measurement for the sample according to the invention and for the conventional samples was calculated for cloth tape and duct tape using the above formula. Without wishing to be bound by theory, it was believed that pendimethalin having an intense staining property, would tend to adsorb strongly on organic surfaces such as polyester, cloth, paper etc. Hence, it was believed that a comparison of the common surfaces such as first aid tape, cloth tape, duct tape would provide a close reflection of actual staining a farmer would encounter as a daily routine.

It was thus surprisingly found that the formulation according to the present invention afforded a substantially non-staining formulation, which was reduced by a fraction of about 5 or at least by a fraction of about 2 comparative to the hitherto known formulation. Specifically, it was surprisingly found that the formulation according to the present invention displayed a staining DE of only 2.44 and 1.49 on cloth tape and duct tape respectively, whereas the closest commercial formulation displayed a staining measurement of 11.22 and 2.19 respectively. Without wishing to be bound by theory, it is believed that the presence of an alkali or alkaline earth metal salt of an organic acid prevents the rupture of the polymeric capsule wall and reduces the staining property of the conventional microencapsulated pendimethalin formulations.

Further staining tests were conducted on various substrates comparing the staining property of the formulations according to the present invention comprising other organic salts of alkali and alkaline earth metals vis-à-vis the formulations comprising an inorganic salt. Again, greater ΔE represented greater staining.

Table 3 demonstrates the cumulative stain value measurements total for cloth tape and first aid tape for a formulation according to the present invention comprising disodium succinate versus a commercially available formulation comprising an inorganic salt, which is further compared to a formulation substantially free of a salt. It was surprisingly found that the formulation comprising disodium succinate (8.600) was only half as staining as the commercially available formulation (16.348).

| ΔE | Cloth Tape | First aid tape | Sum |
|---|---|---|---|
| Commercial formulation | 7.453 | 8.895 | 16.348 |
| No salt | 7.735 | 18.220 | 25.955 |
| Disodium succinate | 4.220 | 4.380 | 8.600 |

($\Delta E_{SD}$ = 0.5)

Figure 1:
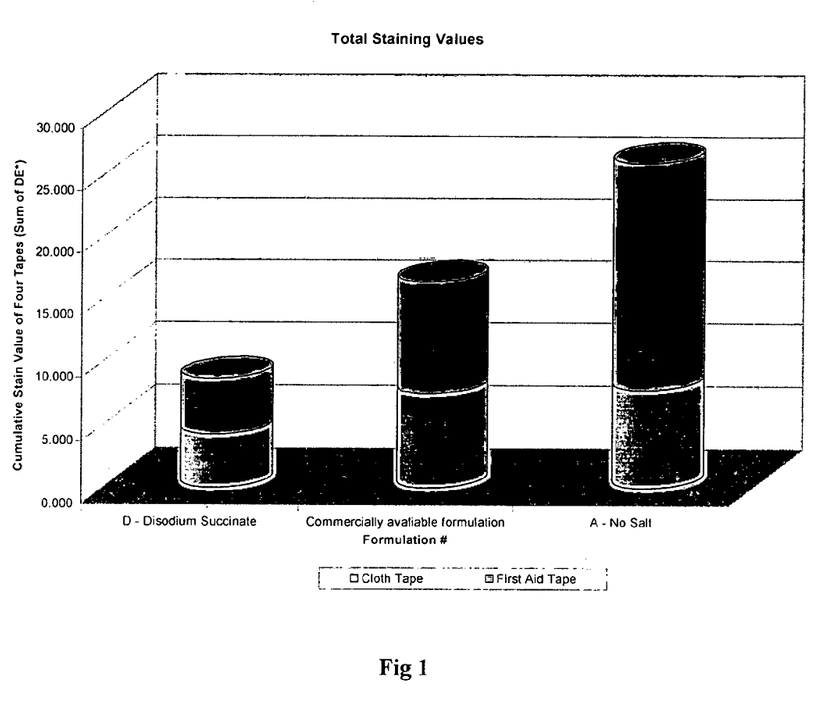
FIG. 1 represents a graphic representation of the data presented in Table 3.

FIG. 1 represents a graphic representation of the data presented in Table 3.

Table 4 demonstrates the stain value measurements total for cloth tape for a formulation according to the present invention comprising sodium acetate versus a commercially available formulation comprising an inorganic salt, which is further compared to a formulation substantially free of a salt. It was surprisingly found that the formulation comprising sodium acetate (2.780) was only a third as staining as the commercially available formulation (7.453).

| ΔE | Cloth tape |
| --- | --- |
| Sodium acetate | 2.780 |
| Commercial formulation | 7.453 |
| No salt | 7.735 |

($\Delta E_{SD}$ = 0.5)

Figure 2:
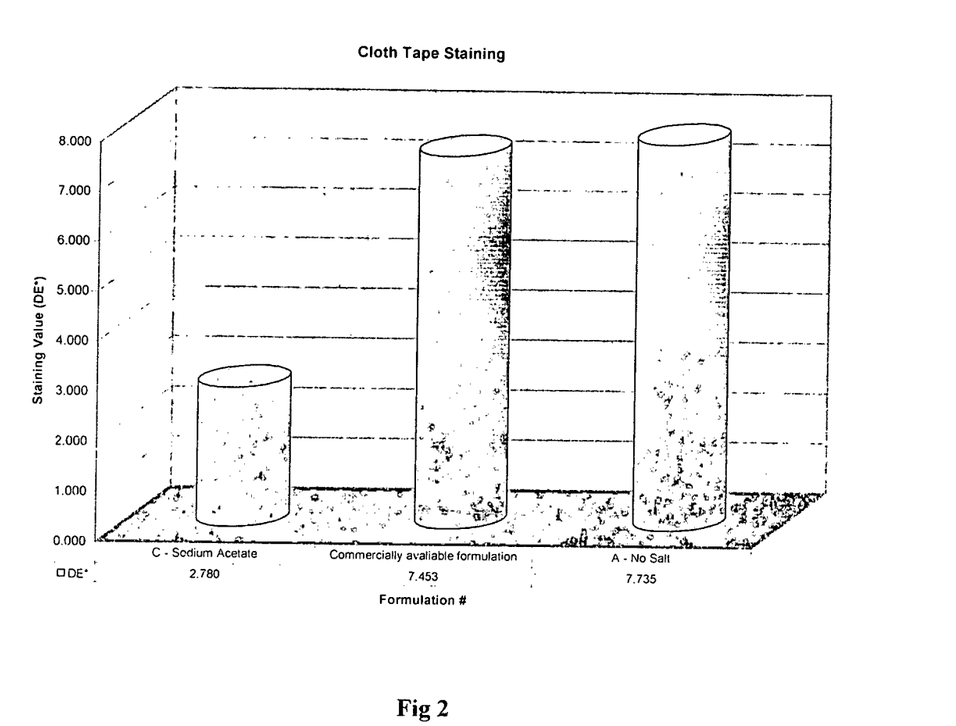
FIG. 2 represents a graphic representation of the data presented in Table 4.

FIG. 2 represents a graphic representation of the data presented in Table 4.

Table 5 demonstrates the stain value measurements for first aid tape for a formulation according to the present invention comprising disodium succinate versus a commercially available formulation comprising an inorganic salt, which is further compared to a formulation substantially free of a salt. It was surprisingly found that the formulation comprising disodium succinate (4.380) was only half as staining as the commercially available formulation (8.895).

| ΔE | First aid tape |
| --- | --- |
| Disodium succinate | 4.380 |
| Commercial formulation | 8.895 |
| No salt | 18.220 |

($\Delta E_{SD}$ = 0.5)

Figure 3:
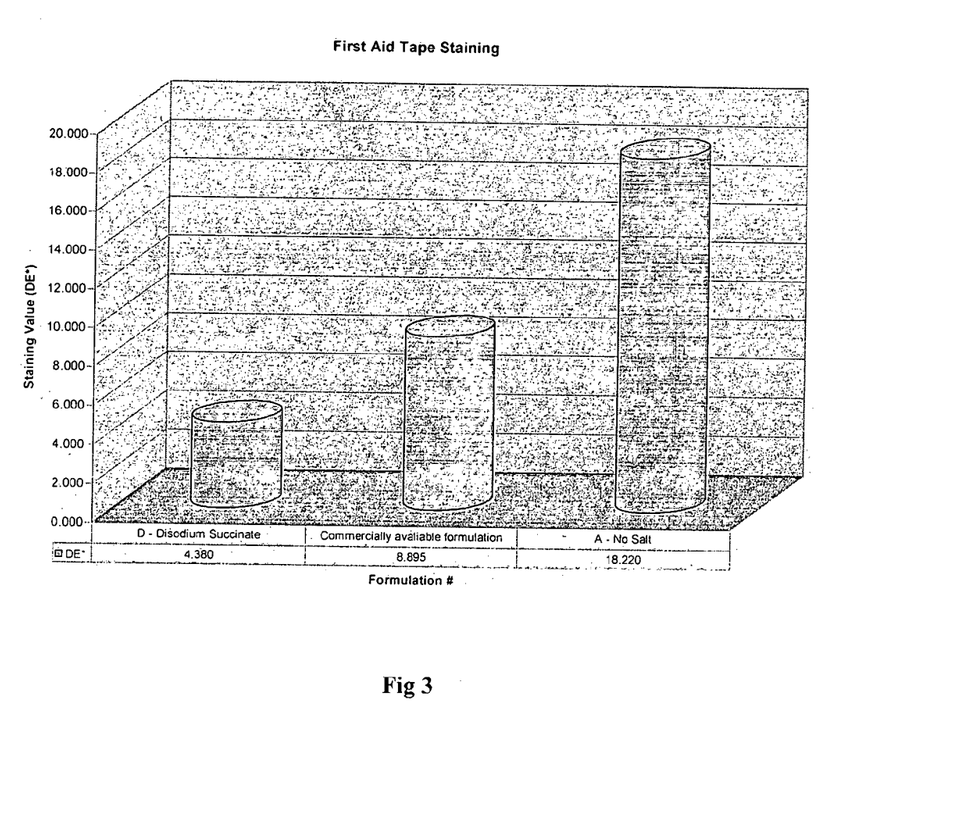
FIG. 3 represents a graphic representation of the data presented in Table 5.

FIG. 3 represents a graphic representation of the data presented in Table 5.

Figure 4:
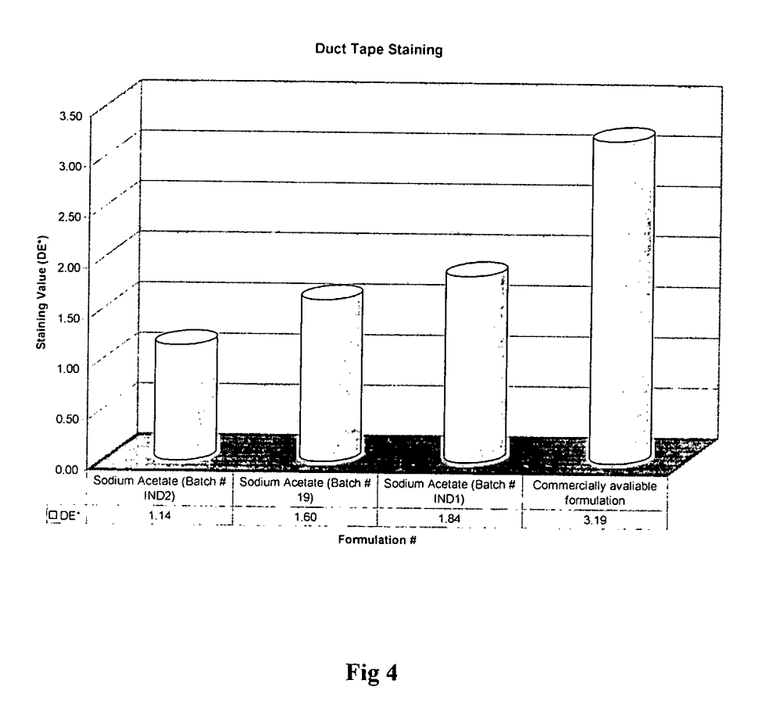
FIG. 4 depicts a comparison of three separate sodium acetate formulations having the same formulation vis-a-vis the staining measured for commercial formulation measured on a duct tape.

FIG. 4 depicts a comparison of three separate sodium acetate formulations having the same formulation vis-à-vis the staining measured for commercial formulation measured on a duct tape. All three batches comprising sodium acetate exhibited ΔE values of 1.14, 1.60 and 1.84 which was only about half of the ΔE exhibited by the commercial formulation, 3.19.

Figure 5:
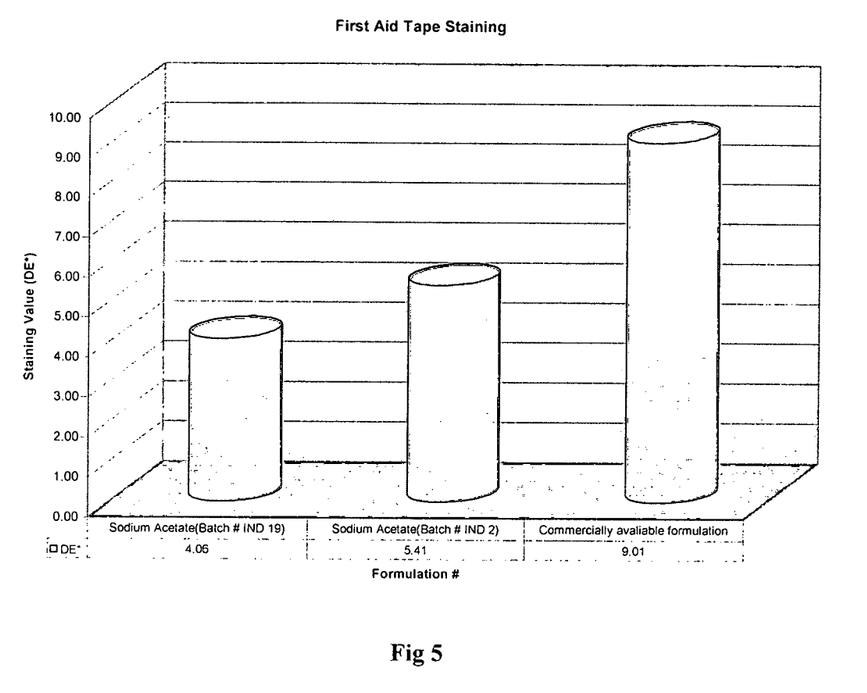
FIG. 5 depicts a comparison of two separate sodium acetate formulations having the same formulation vis-a-vis the staining measured for commercial formulation measured on a first aid tape.

FIG. 5 depicts a comparison of two separate sodium acetate formulations having the same formulation vis-à-vis the staining measured for commercial formulation measured on a first aid tape. The two batches comprising sodium acetate exhibited ΔE values of 4.06 and 5.41 which was only about half of the ΔE exhibited by the commercial formulation, 9.01.

Figure 6:
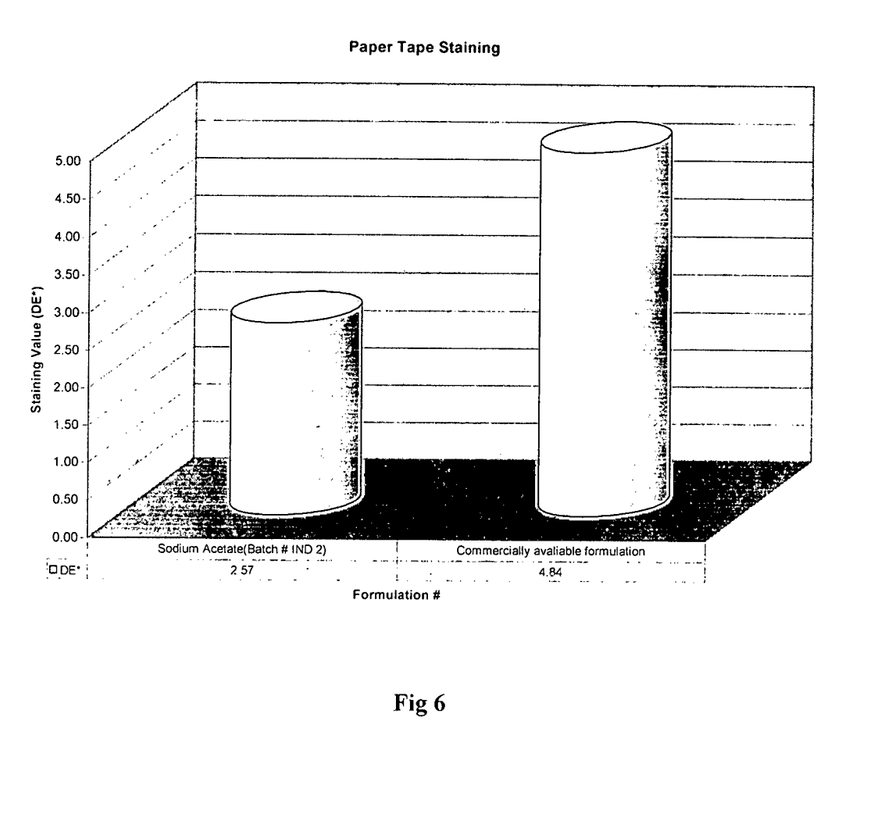
FIG. 6 depicts a comparison of sodium acetate formulation vis-a-vis the staining measured for commercial formulation measured on a paper tape.

FIG. 6 depicts a comparison of sodium acetate formulation vis-à-vis the staining measured for commercial formulation measured on a paper tape. The batch comprising sodium acetate exhibited ΔE values of 2.57 which was only about half of the ΔE exhibited by the commercial formulation, 4.84.

Figure 7:
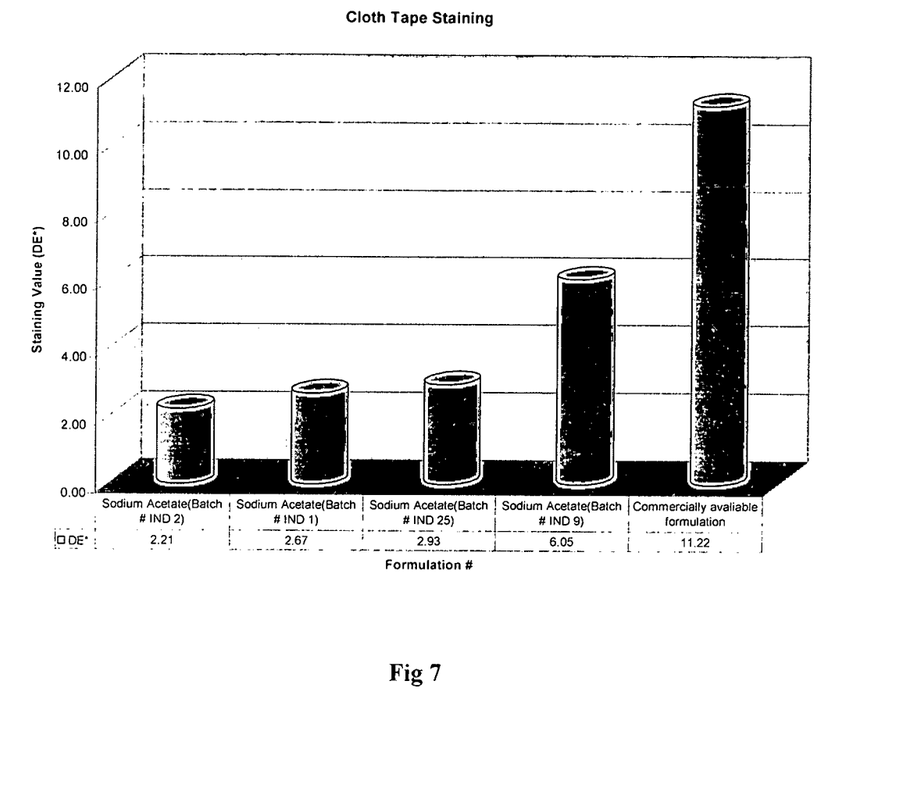
FIG. 7 depicts a comparison of four separate sodium acetate formulations having the same formulation vis-a-vis the staining measured for commercial formulation measured on a cloth tape.

FIG. 7 depicts a comparison of four separate sodium acetate formulations having the same formulation vis-à-vis the staining measured for commercial formulation measured on a cloth tape. The batches comprising sodium acetate exhibited ΔE values of 2.21, 2.67, 2.93 and 6.05 which was only about one-third to about half of the ΔE exhibited by the commercial formulation, 11.22.

Corrosion Resistance

The pendimethalin capsule suspension formulations were prepared comprising about 15% of an organic salt of an alkali or alkaline earth metal, which was compared with the commercial formulation containing 15% sodium chloride. A stainless steel (dimensions: 6 inches by 1.5 inches) strip was placed in the solutions comprising 15% of sodium chloride and compared with formulations containing 15% of sodium acetate, sodium oxalate, sodium succinate, sodium citrate and sodium sulfite respectively. The strips were observed after 24 days storage at room temperature.

It was surprisingly observed that corrosion was observed only in sodium chloride solution whereas the remaining salt solution plates were found corrosion free. The present invention thus readily solves the container corrosion problem which was seen in the currently marketed formulations.

Efficacy

The formulation according to example 3 above was tested against annual grasses and certain broadleaf weeds. Tests were run to investigate the phytotoxicity of the formulations of example 3 of the present invention vis-à-vis the commercially available formulation. The dose of application of the tested formulation was 1-4 quarts/acre prior to weed emergence by diluting it with 10 gallons of water. The formulations were applied using drop nozzles.

Initially, qualitative visual evaluation parameters were tested for phytotoxicity. A numerical plant damage rating scale was used for phytotoxicity determination on a scale of 0 to 10 where 0 represents no phytotoxicity and 10 represents complete "kill". The description of the individual plant scores are as hereunder:

| Rating | Description of plant damage: |
| --- | --- |
| 0 | No damage |
| 1 | No visible damage but unintended non permanent impact |
| 2 | Slight leaf/tissue damage including curling leaves and necrosis |
| 3 | Marginal chlorosis on some leaves damage on up to 10% of plant |
| 4 | 20% Plant damaged |
| 5 | Significant damage to much of plant (30-40%) |
| 6 | 40-60% plant damage |
| 7 | Chlorosis or necrosis on most of plant (60-70%) |
| 8 | Abscised leaves, branch dieback |
| 9 | Tissue severely damaged (80-90%) |
| 10 | Complete kill |

These visual parameters for the evaluation of phytotoxicity were crop lodging, epinasty and hyponasty, stunting of growth, nechrosis, chlorosis or yellowing of crop, leaf blotch or scorching, spotting, rottening, deformation in leaf shape and appearance and twig mortality or leaflet curling. It was surprisingly found that the tested formulations according to the present invention scored over the commercial formulation over all these tested parameters. Apart from the qualitative parameters, the formulations were also tested for the quantitative parameters like the average height of the plant, average number of leaflets in the plant, average fresh and dry weight of the plant and average length/width ratio of the plants. It was surprisingly found that the tested formulations according to the present invention scored over the commercial formulation over all these tested parameters.

The comparative samples were diluted at different doses namely 1×, 2× and 4× along with the control on soybean at three leaf stage. All the doses were sprayed homogenously on plots. Each treatment was observed six times at day 0, 1, 3, 7, 14 and 28 days after treatment. All experiments were replicated thrice to ensure statistical accuracy. It was found that the formulation according to the present invention was substantially non-phytotoxic in comparison to the commercially available formulation.

A phytotoxicity evaluation of formulation without any salt, formulation of Example 3 above vis-à-vis the commercial formulation including an inorganic salt was carried out at 7 days after spraying. The qualitative as well as quantitative parameters were critically observed at appropriate times. It was found that the samples without a salt and that according to example 3 showed similar non-phytotoxic effect on the soyabean plant. These samples were not phyto-toxic at recommended and double recommended doses, whereas at four times recommended dose (4×), the formulation of Example 3 showed only slight phytotoxicity to plant (curling of the leaf edge along with standing of growth). In contrast, the commercially available formulation led to a noticeably higher degree of phytotoxicity than the remaining samples. Further, the plots sprayed with the commercial formulation exhibited less number of plants as compared to corresponding other plots. Further, the growth of the plants were retarded and various other phyto-toxic symptoms like mild chlorosis, necrosis, leaf blotch/scorching and curling of the leaves were observed in dose dependent manner on the commercial formulation sprayed plots.

The observations were repeated at 15$^{th}$ day after application of the sprays. It was observed that in the plots sprayed with the formulation of example 3 and with the formulations without any salt, the plants which showed minor phytotoxicity on the 7$^{th}$ day were found fully recovered from the initial shock. In contrast, a higher degree of necrosis and chlorosis (yellowing of crop) and/or blotching or scorching was observed in the plot sprayed with the commercial formulation even after 15 days of application. The results of the phytotoxicity trials are tabulated as hereunder:

7-Day Testing:

| Parameters | W/O salt 1X | W/O salt 2X | W/O salt 4X | Example 3 1X | Example 3 2X | Example 3 4X | Comm. 1X | Comm. 2X | Comm. 4X |
|---|---|---|---|---|---|---|---|---|---|
| Nechrosis | 2 | 1.5 | 2.5 | 1 | 1 | 2 | 3 | 3.5 | 3.5 |
| Chlorosis | 1.5 | 2.5 | 3 | 1.5 | 2.5 | 3.5 | 3 | 3.5 | 5 |
| Blotching or scorching | 2.5 | 3.5 | 3.5 | 2.5 | 3.5 | 3 | 4.5 | 5.5 | 7 |
| Plant height (cm, ave.) Control = 10.3 cm | 8.78 | 8.45 | 8.30 | 10.38 | 9.60 | 9.20 | 7.20 | 7.0 | 6.95 |

15-Day Testing:

| Parameters | W/O salt 1X | W/O salt 2X | W/O salt 4X | Example 3 1X | Example 3 2X | Example 3 4X | Comm. 1X | Comm. 2X | Comm. 4X |
|---|---|---|---|---|---|---|---|---|---|
| Nechrosis | 2 | 2.5 | 2 | 1.5 | 1.5 | 2 | 3 | 3 | 4 |
| Chlorosis | 3 | 3.5 | 3 | 2 | 4 | 3 | 4.5 | 5.5 | 6 |
| Blotching or scorching | 3.5 | 5 | 4 | 4 | 4.5 | 4.5 | 4.5 | 5 | 6.5 |
| Plant height (cm, ave.) Control = 17.0 cm | 15.0 | 13.05 | 12.20 | 14.95 | 13.75 | 11.8 | 11.55 | 9.95 | 9.55 |

Thus, it was found that the formulations according to an embodiment of the present invention as well as a formulation without any salt were substantially less phytotoxic, showed substantially less plant growth stunting as compared to a commercially available formulation.

| | Average number of plant growth/Per plot | | | | | | | | |
|---|---|---|---|---|---|---|---|---|---|
| Parameters | W/O salt 1X | W/O salt 2X | W/O salt 4X | Example 3 1X | Example 3 2X | Example 3 4X | Comm. 1X | Comm. 2X | Comm. 4X |
| Average number of plant growth (control = 145) | 132 | 128.5 | 111 | 142.5 | 144 | 124.5 | 110 | 115 | 105 |

It was found that the maximum density of plant growth was observed in the plot that was sprayed with the formulation of example 3, which was almost comparable to the control plot or the plot sprayed with the formulation without any salt. Surprisingly, the plots sprayed with the commercial sample displayed the least plant growth density. It was surprising that the presence of an alkali or alkaline earth metal salt of an organic acid could lead to a substantial increase in the plant growth density.

Wherein the aforegoing reference has been made to components having known equivalents, then such equivalents are herein incorporated as if individually set forth.

Accordingly, it will be appreciated that changes may be made to the above described aspects and embodiments of the invention without departing from the principles taught herein. Additional advantages of the present invention will become apparent for those skilled in the art after considering the principles in particular form as discussed and illustrated. Thus, it will be understood that the invention is not limited to the particular embodiments described or illustrated, but is intended to cover all alterations or modifications which are within the scope of the invention.

The invention claimed is:

1. A capsule suspension formulation of pendimethalin comprising microcapsules comprising pendimethalin encapsulated within a polymeric wall formed in-situ by an interfacial polymerization reaction occurring between an organic phase dispersed in an aqueous phase, said aqueous phase comprising at least one alkali or alkaline earth metal salt of an organic acid, wherein said organic acid is selected from the group consisting of acetic acid, propionic acid, citric acid, fumaric acid, tartaric acid, oxalic acid, succinic acid, valeric acid, malonic acid, glutaric acid, adipic acid and phthalic acid, with the proviso that the aqueous phase does not comprise an inorganic salt prior to formation of the polymeric wall, wherein the formulation comprises about 5% to about 60% pendimethalin by weight, about 1% to about 20% polymeric wall by weight, and about 2% to about 55% the at least one alkali or alkaline earth metal salt of an organic acid by weight.

2. The formulation as claimed in claim 1, having a reduced staining property over an encapsulated pendimethalin formulation comprising an inorganic salt within the microcapsule.

3. The formulation as claimed in claim 1, wherein said polymeric wall is selected the group consisting of polyurea, polyurethane, polyamide, polycarbonate, polysulfonamide and crosslinked or non-crosslinked combinations thereof.

4. The formulation as claimed in claim 3, wherein the polymeric wall is a polyurea wall.

5. The formulation as claimed in claim 1, wherein said polymeric wall is formed by an interfacial polymerization triggered by contacting a first wall forming component with a second wall forming component.

6. The formulation as claimed in claim 5, wherein said first and second wall forming components, being same or different, are included within at least one of said organic and aqueous phases.

7. The formulation as claimed in claim 5, wherein said first wall forming component is selected from the group consisting of polyisocyanate, polyacid chloride, polychloroformate and polysulfonyl chloride.

8. The formulation as claimed in claim 5, wherein said second wall forming component is selected from the group consisting of polyamine and polyol.

9. The formulation as claimed in claim 7, wherein said first wall forming component is selected from the group consisting of tetramethylene diisocyanate, pentamethylene diisocyanate, hexamethylene diisocyanate, toluene diisocyanate, diphenylmethene-4,4'-diisocyanate, polymethylene polyphenylene isocynate, 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4'4"-triphenylmethane triisocyanate.

10. The formulation as claimed in claim 5, wherein said first wall forming component is present in an amount of about 0.1% to about 20% by weight of the organic phase.

11. The formulation as claimed in claim 5, wherein said second wall forming component is present in an amount of about 0.3% to 7.5% by weight relative to the total weight of the formulation.

12. The formulation as claimed in claim 4, wherein said polyurea wall is formed by a self-condensation reaction of a polyisocyanate wall forming component.

13. The formulation as claimed in claim 1, wherein said alkali or alkaline earth metal moiety of said alkali or alkaline earth metal salt of an organic acid is selected from the group consisting of sodium and potassium.

14. The formulation as claimed in claim 1, wherein said alkali or alkaline earth metal salt of an organic acid is sodium acetate or disodium succinate.

15. The formulation as claimed in claim 1, wherein said microcapsules have a particle size of about 2 micrometers to about 50 micrometers.

16. The formulation as claimed in claim 1 further comprising at least one excipient selected from the group consisting of an anti-foam in an amount of about 0.01% to about 5% by weight of the formulation, a rheology modifier in an amount of about 0.01% to about 3% by weight of the formulation, a mineral acid from about 0.1% to about 10% by weight of the formulation and a biocide in an amount of from about 0.01% to about 3% by weight of the formulation.

17. A capsule suspension formulation of pendimethalin comprising from about 5% to about 60% of pendimethalin active ingredient by weight, said pendimethalin being encapsulated within a microcapsule comprising a polyurea wall comprising from about 1% by weight to about 20% by weight of the formulation, said polyurea wall being in-situ formed by an interfacial polymerization reaction occurring between an organic phase dispersed in an aqueous phase, said organic phase comprising a polyisocyanate wall forming component and said aqueous phase being characterized in consisting essentially of a pre-defined amount of a salt selected from sodium acetate or disodium succinate, with the proviso that the aqueous phase does not comprise an inorganic salt prior to formation of the polyurea wall.

18. A method for controlling undesirable plant species at a locus, said method comprising applying to the desired locus a herbicidally effective amount of a formulation as claimed in claim 1.

* * * * *